United States Patent [19]

Kobayashi et al.

[11] 4,260,986
[45] Apr. 7, 1981

[54] TOOL WEAR DETECTING SYSTEM FOR A NUMERICALLY CONTROLLED MACHINE TOOL

[75] Inventors: Kengo Kobayashi, Kawasaki, Japan; Yasunobu Sawada, Elk Groove Village, Ill.

[73] Assignee: Fujitsu Fanuc Limited

[21] Appl. No.: 32,696

[22] Filed: Apr. 23, 1979

[30] Foreign Application Priority Data

Apr. 26, 1978 [JP] Japan .................................. 53-49412

[51] Int. Cl.³ ........................................... G08B 21/00
[52] U.S. Cl. ..................................... 340/680; 73/104; 235/421; 408/11
[58] Field of Search ................ 340/680, 664; 235/301, 235/421; 408/11, 6, 16; 73/104

[56] References Cited

U.S. PATENT DOCUMENTS

| | | | |
|---|---|---|---|
| 3,545,310 | 12/1970 | Porath et al. | 408/11 |
| 3,596,544 | 8/1971 | Pitman | 340/680 |
| 3,809,870 | 5/1974 | Auble et al. | 73/104 |
| 3,841,149 | 10/1974 | Edwin et al. | 73/104 |
| 3,930,248 | 12/1975 | Keller | 340/680 |
| 3,962,694 | 6/1976 | Calia et al. | 340/680 |
| 4,023,044 | 5/1977 | Miller et al. | 340/680 |
| 4,076,442 | 2/1978 | Cox, Jr. et al. | 408/11 |
| 4,087,801 | 5/1978 | Noh | 73/104 |
| 4,090,403 | 5/1978 | Tsukada et al. | 73/104 |
| 4,207,567 | 6/1980 | Juengel et al. | 340/680 |

*Primary Examiner*—Glen R. Swann, III
*Attorney, Agent, or Firm*—Staas & Halsey

[57] ABSTRACT

A numerically controlled machine tool controls the movement of a tool relative to a workpiece along a commanded path to cut the workpiece and to detect a load on the tool or workpiece. A specified position or section on the commanded path is the point at which the load on the tool or workpiece is detected and stored. Subsequently, the load on the tool or workpiece is detected each time the tool passes through the specified position or section and this detected value is compared with the above stored content. When the difference is larger than a predetermined value, an alarm signal is produced to indicate that the tool has worn out.

9 Claims, 3 Drawing Figures

TOOL WEAR DETECTING SYSTEM FOR A NUMERICALLY CONTROLLED MACHINE TOOL

BACKGROUND OF THE INVENTION

1. Field of the Invention

This invention relates to a tool wear detecting system which detects wear of a cutter in a numerically controlled machine tool during cutting.

2. Description of the Prior Art

A cutter of a machine tool is used for cutting a workpiece and gradually wears away and must be reground or replaced with a new cutter. In a numerically controlled machine tool, a tool shift command is provided from a numerical control unit, so that even if the cutter has worn away, the depth of cut and the feed rate of the cutter are not altered. Accordingly, when the cutter has worn away, the load on the tool or the workpiece markedly increases and if cutting continues, the tool may in some cases be broken. Once the tool has thus been broken it cannot be reground for further use.

There has been proposed a numerically controlled machine tool combined with an adaptive control. The adaptive control is adapted to control the feed rate, etc. of the tool so that the load on the tool or workpiece does not exceed an allowable value. Such a machine tool is free from the abovementioned defect leading to the tool breakage but has the defect of complex and expensive structure.

SUMMARY OF THE INVENTION

An object of this invention is to provide a tool wear detecting system, which detects wear of a cutting tool, employing a simple structure.

Another object of this invention is to provide a tool wear detecting system which detects a load on a cutting tool or a workpiece, thereby detecting wear of the cutting tool.

Briefly, in the tool wear detecting system of this invention, a load on a cutting tool or workpiece is detected at a specified position or in a specified section and stored. Thereafter a load on the cutting tool or workpiece is detected each time the cutting tool passes through the abovementioned position or section and the detected load is compared with the above-mentioned stored content; when the difference between them is larger than a predetermined value, an alarm signal is outputted to give notice of the wear of the cutting tool.

DESCRIPTION OF THE PREFERRED EMBODIMENTS

In ordinary machining of a workpiece a material having a casting skin is worked by a plurality of cutting processes into a desired, predetermined configuration. In this case, a required depth of cut is set prior to each cutting process. Accordingly, after the roughness of the material surface is removed, a constant depth cut is repeated. In the case where the workpiece cutting is achieved at a constant depth of cut and a constant feed rate, if the cutting tool does not wear, a load on the cutting tool or the work can be regarded as constant throughout all of the cutting processes. As the cutting tool becomes worn, the cutting ability of the tool deteriorates, so that the load on the tool or work increases.

In this invention, on the basis of the increase in the load on the tool or work owing to the wear of the tool, the load on the tool or work at a specified position or in a specified section along a commanded path of the tool is detected and stored. In each of the subsequent processes, the load on the tool or work at the position or in the section corresponding to the abovesaid one is detected for comparison with the stored content and if the difference between them is larger than a predetermined value, a signal is provided to indicate that the tool should be replaced with a new one.

Figure 1:
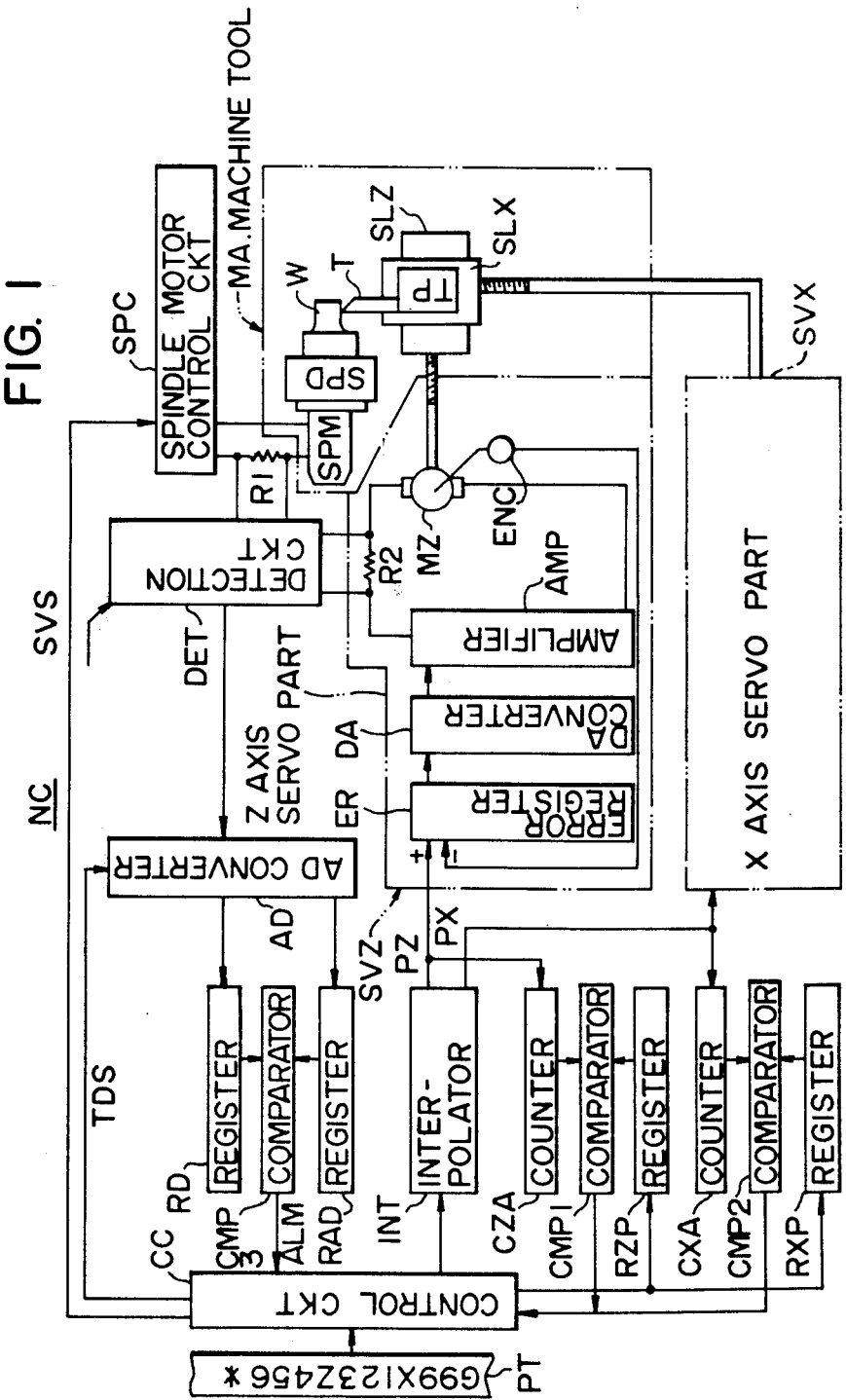
FIG. 1 is a block diagram showing a numerically controlled machine tool employing one embodiment of this invention.

In FIG. 1, reference character NC indicates a numerical control unit; PT designates a command tape; CC identifies a control circuit; INT denotes an interpolator; RD, RAD, RZP and RXP represent registers; CZA and CXA show counters; CMP1 through CMP3 refer to comparators; SVZ indicates a Z-axis servo part; ER designates an error register; DA identifies a D-A converter; AMP denotes an amplifier; MZ represents a Z-axis feed motor; ENC shows a Z-axis pulse encoder; SVX refers to an X-axis servo part; SPC indicates a spindle motor control circuit; DET designates a detection circuit; AD identifies an A-D converter; R1 and R2 denote resistors; MA identifies a machine tool; SPD denotes a spindle; SPM represents a spindle motor; W shows a workpiece; T refers to a tool; TP indicates a tool post; SLZ designates a Z-axis slide rest; and SLX identifies an X-axis slide rest.

In an ordinary numerical control operation, the control circuit CC responds to spindle command data from the command tape PT to apply a spindle speed command SVS to the spindle motor control circuit SPC to drive the spindle motor SPM at the commanded speed. Further, the control circuit CC provides X- and Z-axis command data to the interpolator INT to accomplish pulse distribution, by which distribution pulses PX and PZ are provided to the respective axis servo parts SVX and SVZ to move the tool T relative to the workpiece W via the slides SLX and SLZ, respectively.

The distribution pulses PX and PZ are respectively stored in current position counters CXA and CZA. In the present embodiment, to detect a load on the tool T or the workpiece W, a load current of the spindle motor SPM is detected by the detector DET as a voltage drop across the resistor R1.

Figure 2:
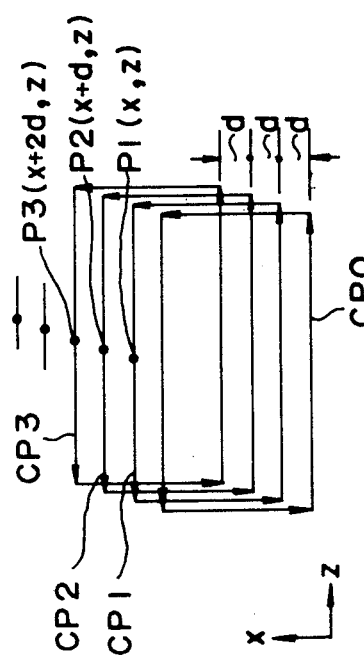
FIG. 2 explains the paths of a cutting tool in respective processes.

Together with command data representing a command path CP0 shown in FIG. 2, a specified position in one process, given a specific code, for example, G99, is assigned on the command tape PT, with a co-ordinate value (x, z) as X123Z456.

Upon reading the above-mentioned specific code indicating readout and storage of the load torque of the tool and specified position data (the co-ordinate value (x, z) of a position P1 in FIG. 2), the control circuit CC sets co-ordinate values of respective axes in the registers RZP and RXP.

Next, a shift command is executed and when the current position of the tool T has reached the position P1 in FIG. 2, the comparators CMP1 and CMP2 both provide coincidence signals and the control circuit CC applies a read signal TDS to the A-D converter AD to convert a detection signal from the detector DET to a digital signal, which is set in the register RD. The register RD indicates the load torque of the tool at the position P1.

Then, upon completion of the first process, cutting to the same depth d as in the first process is accomplished in the next process. At this time, the content of the X-axis register RXP is corrected by d.

In a second process, when the tool T has reached a specified position P2 corresponding to the aforementioned one P1, that is, a position spaced a distance from the position P1 in a direction +X corresponding to the depth of cut d, the comparators CMP1 and CMP2 yield coincidence signals again and the detected output from the detector DET is set via the A-D converter AD in the register RAD. In the comparator CMP3, the following decision takes place:

$$(RAD)-(RD) \geq Q$$

If the equation is not satisfied, the same operations as mentioned above are repeated. If the equation is satisfied, an alarm signal ALM is provided to the control circuit CC to stop the subsequent operation. Q is a predetermined allowable load torque difference, which is predetermined in dependence upon the materials of the tool and the workpiece and is preset in the comparator CMP3.

The load on the tool or workpiece can also be detected by detecting the load current of the Z-axis feed motor MZ as a voltage drop across the resistor R2 by the detector DET. Further, it is also possible to provide a strain gauge on the tool T and apply its output signal to the A-D converter AD. In the case of a computer numerical control unit (CNC), the counters and the registers can also be provided in areas of a memory and the functions of the comparators can also be replaced with calculation, comparison and decision functions of a central processing unit.

Figure 3:
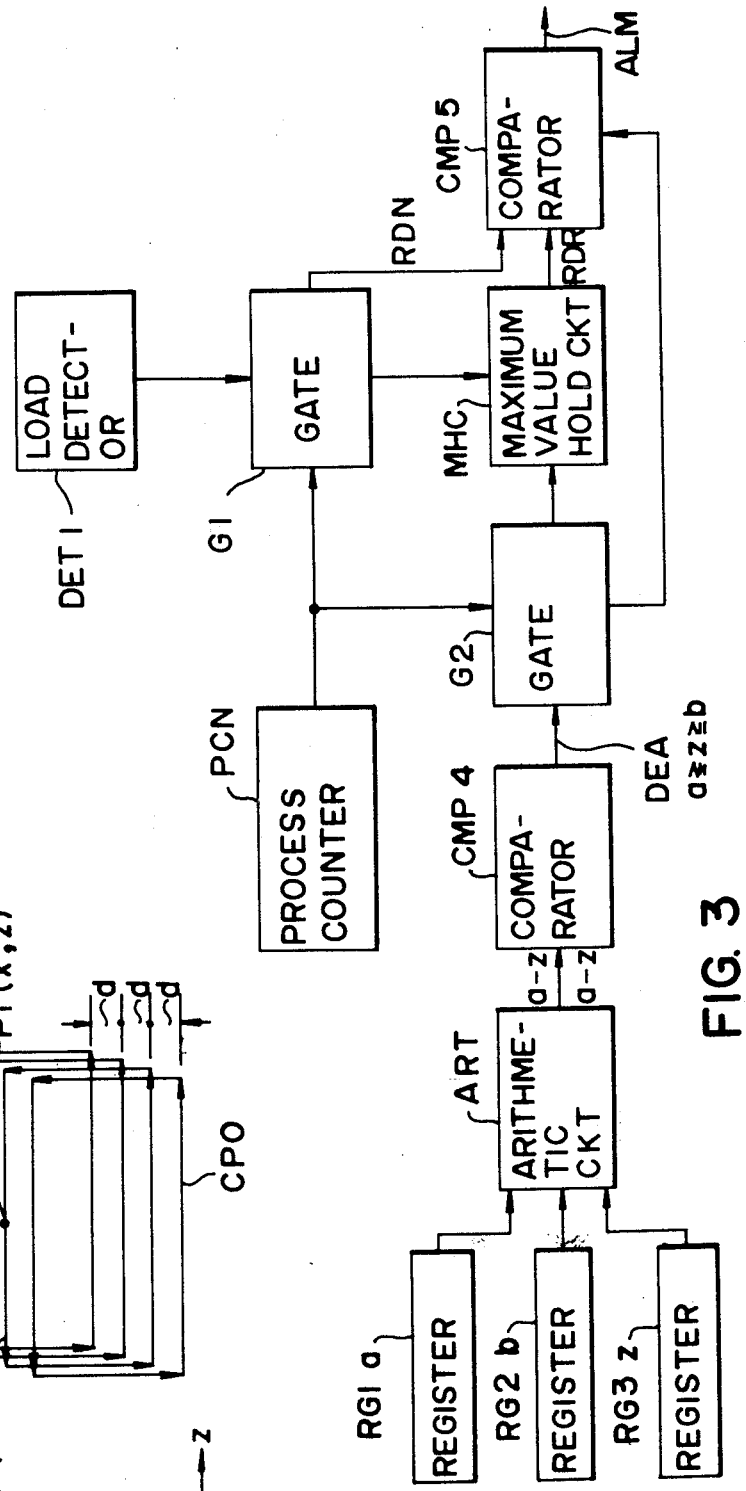
FIG. 3 is a block diagram showing the principal part of another embodiment of this invention.

FIG. 3 shows in block form the principal part of another embodiment of this invention. In FIG. 3, reference characters RG1 through RG3 indicate registers; ART designates an arithmetic circuit; CMP4 identifies a comparator; CMP5 denotes an analog comparator; DET1 represents a load detector for a tool or work; PCN shows a process counter; G1 and G2 refer to gates; and MHC indicates a maximum value hold circuit.

In the present embodiment, a section ($a \geq x \geq b$ for detecting and comparing a load on the tool or workpiece is assigned in the registers RG1 and RG2, and when the content z of the Z-axis current value register RG3 exists in the above-mentioned section, an in-section signal DEA is yielded via the arithmetic circuit ART and the comparator CMP4.

The process counter PCN counts the number of cutting processes and, in a first process, controls the gate G1 to apply therethrough the output from the detector DET1 to the maximum value hold circuit MHC. The maximum value hold circuit MHC holds a maximum value RDR of the output from the detector DET1 while the signal DEA provided via the gate G2 lasts.

Upon completion of the first process, the process counter PCN advances by one step to start control of a second process. In the second and subsequent processes, the gates G1 and G2 are both changed over; namely, the output from the detector DET1 is applied via the gate G1 to the comparator CMP5 and the signal DEA is applied via the gate G2 to the comparator CMP5. The comparator CMP5 compares the load data RDR stored in the maximum value hold circuit MHC with newly detected load data RDN while the signal DEA lasts, and produces an alarm signal ALM when $RDN-RDR \geq Q$. Also in this case, Q is preset in the comparator CMP5 as is the case with the foregoing embodiment.

As has been described in the foregoing, according to this invention, the load torque of the tool at a specified position or in a specified section in one process is stored and compared with the load torque of the tool at the corresponding position or in the corresponding section in the subsequent processes to determine the load torque difference and, to generate an alarm signal if the difference is abnormal; therefore, the wear of the tool can easily be detected by simple means, thereby ensuring that breakage of the tool is prevented.

It will be apparent that many modifications and variations may be effected without departing from the scope of the novel concepts of this invention.

What is claimed is:

1. A tool wear detecting system for a numerically controlled machine tool, which controls the movement of a tool relative to a workpiece along a commanded path to cut the workpiece, comprising means for detecting a load on the tool or workpiece,
   wherein a position on or section of the commanded path is specified in advance and the load on the tool or workpiece at the time the tool passes through the specified position or section during an initial process is detected by the detecting means; storage means, operatively connected to said detecting means, for storing the load detected by said detecting means; and comparator means, operatively connected to said detecting means and said storage means,
   wherein in each of the subsequent processes, the load on the tool or workpiece, at the time the tool passes through the position or section corresponding to the specified position or section, is detected by the detecting means and the detected data is compared with the data stored in the storage means and when the difference between them is larger than a predetermined value, an alarm signal is produced to indicate that the tool is worn out.

2. A tool wear detecting system according to claim 1, wherein a maximum value of the load on the tool or workpiece at the time the tool passes through the specified section on the commanded path during an initial process is stored in the storage means, and wherein in each of the subsequent processes, the value of the load on the tool or workpiece at the time the tool passes through the section corresponding to the specified section is detected and compared with the maximum value stored in the storage means.

3. A tool wear detecting system for a machine tool having a numerical control unit which controls the movement of a tool relative to a workpiece, said tool driven by motors and moved along a commanded path to cut the workpiece, comprising:
   detecting means, operatively connected to the machine tool, for detecting a load on the tool at the time the tool passes a specified position on the commanded path;
   storage means, operatively connected to said detecting means and to the numerical control unit, for storing, as load data, the load detected by said detecting means when the tool passes the specified position on the commanded path for the first time and for storing, as present data, the load detected by said detecting means when the tool passes the specified position on the commanded path at a subsequent time; and an alarm comparator circuit, having an alarm value stored therein, operatively connected to said storage means, for comparing said present data with said load data, and for providing an alarm signal if said present data is greater than or equal to the sum of said alarm value and said load data, whereby the alarm signal indicates that the tool is worn out.

4. A tool wear detecting system as set forth in claim 3, wherein said detecting means comprises a detection circuit, operatively connected to a first of the tool driving motors, for detecting the load current of the first tool driving motor and for outputting a detection signal.

5. A tool wear detecting system as set forth in claim 4, wherein said storage means comprises:

first and second registers, operatively connected to the numerical control unit, for storing first and second coordinate axis values, respectively, representing said specified position on the commanded path;

an interpolator circuit, operatively connected to the numerical control unit, for providing first and second trains of distribution pulses to control movement of the tool;

first and second counters, operatively connected to said interpolator circuit, for counting said first and second distribution pulses, respectively, said first counter containing the present first axis value and said second counter containing a present second axis value;

a first comparator circuit, operatively connected to said first counter, said first register and the numerical control unit, for providing a first coincidence signal when said first coordinate axis value and said present first axis value coincide;

a second comparator circuit, operatively connected to said second register, said second counter and the numerical control unit, for providing a second coincidence signal when said second coordinate axis value and said present first axis value coincide;

an analog to digital converter, operatively connected to said detection circuit and the numerical control unit, for providing a digital detection signal every time a read signal is received from the numerical control unit, said read signal being provided when the numerical control unit receives said first coincidence signal and said second coincidence signal concurrently;

a third register, operatively connected to said analog to digital converter and to said alarm comparator circuit, for storing said digital detection signal as said load data the first time the tool passes the position specified by said first and second coordinate axis values; and a fourth register, operatively connected to said analog to digital converter and to said alarm comparator circuit, for storing said digital detection signal as said present data every time the tool passes the position specified by said first and second coordinate axis values subsequent to the first time.

6. A tool wear detecting system for a machine tool having a numerical control unit which controls the movement of a tool relative to a workpiece, said tool moved along a commanded path to cut the workpiece, said workpiece driven by a spindle motor, comprising:

detecting means, operatively connected to the workpiece, for detecting a load on the workpiece at the time the tool passes a specified position on the commanded path;

storage means, operatively connected to said detecting means and to the numerical control unit, for storing, as load data, the load detected by said detecting means when the tool passes the specified position on the commanded path for the first time and for storing, as present data, the load detected by said detecting means when the tool passes the specified position on the commanded path at a subsequent time; and an alarm comparator circuit, having an alarm value stored therein, operatively connected to said storage means, for comparing said present data with said load data, and for providing an alarm signal if said present data is greater than or equal to the sum of said alarm value and said load data, whereby the alarm signal indicates that the tool is worn out.

7. A tool wear detecting system as set forth in claim 6, wherein said detecting means comprises a detection circuit, operatively connected to the spindle motor, for detecting the load current of the spindle motor and for outputting a detection signal.

8. A tool wear detecting system for a machine tool having a numerical control unit which controls the movement of a tool relative to a workpiece, said tool moved along a commanded path to cut the workpiece, said tool wear detecting system comprising:

a load detector circuit, operatively connected to the machine tool, for detecting a load on the tool and for providing a detection signal;

storage and gating means, operatively connected to the load detector circuit, for storing, as maximum value data, the maximum value of the load detected by said load detector circuit when the tool passes through a specified section of the commanded path for the first time and for providing as present data the load detected by said load detector circuit when the tool passes through said specified section of the commanded path at a subsequent time; and an alarm comparator circuit, having an alarm value stored therein, operatively connected to said storage and gating means, for comparing said present data with said maximum data, and for providing an alarm signal if said present data is greater than or equal to the sum of said alarm value and said maximum value data, whereby the alarm signal indicates that the tool is worn out.

9. A tool wear detecting system as set forth in claim 8, wherein said storage means comprises:

a process counter circuit, operatively connected to the machine tool, for counting the number of cutting processes which the machine tool has made and for providing a first process signal the first time the machine tool performs a cutting process and for providing a subsequent process signal for all subsequent cutting processes;

a first register for storing a first range value;

a second register for storing a second range value;

a third register, operatively connected to the machine tool, for storing a current axis value;

comparison means, operatively connected to said first, second and third registers, for providing an inspection signal if said current axis value is greater than or equal to said second range value and less than or equal to first range value;

a first gate, operatively connected to said load detector circuit and to said process counter circuit, for providing as an output said detection signal in the form of said maximum value signal when said first process signal is received and for providing as an output said detection signal in the form of said present data signal when said subsequent process signal is received;

a second gate, operatively connected to said process counter circuit and said comparison means, for providing a first in-section signal output when said first process signal is received and for providing a second in-section signal output when said subsequent process signal is received; and a maximum value hold circuit, operatively connected to said first and second gates and to said alarm comparator circuit, for storing said maximum value signal and for providing said maximum value signal to said alarm comparator circuit.

* * * * *

UNITED STATES PATENT AND TRADEMARK OFFICE
CERTIFICATE OF CORRECTION

PATENT NO. : 4,260,986
DATED : April 7, 1981
INVENTOR(S) : KENGO KOBAYASHI ET AL.

It is certified that error appears in the above—identified patent and that said Letters Patent is hereby corrected as shown below:

Front page, [75], Inventors, line 2, "Elk" should be --EIK--.

Col. 1, line 27, "abovementioned" should be --above-mentioned--;
       line 42, after "Thereafter" insert --,--;
       line 44, "abovementioned" should be --above-mentioned--.

Col. 3, line 43, "work" should be --workpiece--;
       line 47, "x" should be --z--;
       line 47, after "b" insert --)--.

Col. 4, line 13, after "and" delete ",".

Signed and Sealed this

Eighteenth Day of August 1981

[SEAL]

Attest:

GERALD J. MOSSINGHOFF

Attesting Officer

Commissioner of Patents and Trademarks